(12) United States Patent
Masumura (10) Patent No.: US 10,433,734 B2
(45) Date of Patent: Oct. 8, 2019

(54) APPARATUS AND METHOD FOR IRRADIATING A MEDIUM

(71) Applicant: CANON KABUSHIKI KAISHA, Tokyo (JP)

(72) Inventor: Takahiro Masumura, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/708,062

(22) Filed: May 8, 2015

(65) Prior Publication Data

US 2015/0238092 A1 Aug. 27, 2015

Related U.S. Application Data

(63) Continuation of application No. 12/566,592, filed on Sep. 24, 2009, now Pat. No. 9,057,695.

(51) Int. Cl.
*A61B 5/00* (2006.01)
*G01N 21/47* (2006.01)
(Continued)

(52) U.S. Cl.
CPC ....... *A61B 5/0097* (2013.01); *G01N 21/1717* (2013.01); *G01N 21/4795* (2013.01); *G03H 1/02* (2013.01); *G03H 1/04* (2013.01); *G03H 1/2205* (2013.01); *G03H 1/2645* (2013.01); *G03H 1/28* (2013.01); *G01N 2021/1727* (2013.01); *G03H 1/0005* (2013.01); *G03H 2001/0212* (2013.01);
(Continued)

(58) Field of Classification Search
USPC ........ 600/437, 473, 476; 359/10, 11, 22, 32; 356/450–521; 73/603
See application file for complete search history.

(56) References Cited

U.S. PATENT DOCUMENTS 3,715,482 A * 2/1973 Haines et al. ............. 367/8
4,284,324 A * 8/1981 Huignard ............. G01H 9/002
359/30

(Continued)

FOREIGN PATENT DOCUMENTS

CN 1415083 A 4/2003
CN 1681016 A 10/2005
(Continued)

OTHER PUBLICATIONS

Yaqoob et al., "Optical Phase Conjugation for Turbidity Suppression in Biological Samples", published in Nat. Photnoics 2 (2), pp. 110-115 (Year: 2008).*

(Continued)

*Primary Examiner* — James M Kish
(74) *Attorney, Agent, or Firm* — Canon U.S.A., Inc. IP Division (57) ABSTRACT

A method for irradiating a medium includes irradiating the medium with an electromagnetic wave which is scattered in the medium and modulated in frequency at a position in the medium; obtaining information corresponding to an interference pattern generated by interference between the modulated electromagnetic wave and a reference wave; and generating a phase conjugate wave, based on the obtained information, which irradiates the medium.

19 Claims, 9 Drawing Sheets

(51) Int. Cl.
*G03H 1/02* (2006.01)
*G03H 1/04* (2006.01)
*G03H 1/26* (2006.01)
*G03H 1/28* (2006.01)
*G03H 1/22* (2006.01)
*G01N 21/17* (2006.01)
*G03H 1/00* (2006.01)

(52) U.S. Cl.
CPC ........... *G03H 2001/0467* (2013.01); *G03H 2001/2213* (2013.01); *G03H 2001/2244* (2013.01); *G03H 2001/2655* (2013.01); *G03H 2210/62* (2013.01); *G03H 2222/10* (2013.01); *G03H 2260/36* (2013.01)

(56) References Cited

U.S. PATENT DOCUMENTS

| | | | |
|---|---|---|---|
| 4,385,634 A * | 5/1983 | Bowen | 600/407 |
| 4,622,843 A * | 11/1986 | Hormel | 73/1.76 |
| 5,293,873 A * | 3/1994 | Fang | 600/437 |
| 5,424,843 A * | 6/1995 | Tromberg et al. | 356/442 |
| 5,441,054 A * | 8/1995 | Tsuchiya | 600/310 |
| 5,477,051 A * | 12/1995 | Tsuchiya | 250/341.1 |
| 5,517,987 A * | 5/1996 | Tsuchiya | 600/328 |
| 5,548,301 A * | 8/1996 | Kornher | G09G 3/2022 345/205 |
| 5,713,356 A * | 2/1998 | Kruger | 600/407 |
| 5,840,023 A * | 11/1998 | Oraevsky et al. | 600/407 |
| 6,134,006 A * | 10/2000 | Telschow et al. | 356/503 |
| 6,377,367 B1 * | 4/2002 | Suganuma | 359/1 |
| 6,653,421 B1 * | 11/2003 | Yamamoto et al. | 526/259 |
| 6,738,653 B1 * | 5/2004 | Sfez et al. | 600/322 |
| 6,957,096 B2 * | 10/2005 | Sfez et al. | 600/407 |
| 2002/0057486 A1 * | 5/2002 | Tanaka | 359/292 |
| 2005/0107694 A1 * | 5/2005 | Jansen et al. | 600/431 |
| 2005/0231775 A1 * | 10/2005 | Kubota et al. | 359/15 |
| 2006/0058685 A1 * | 3/2006 | Fomitchov et al. | 600/476 |
| 2007/0187632 A1 * | 8/2007 | Igarashi | 250/559.36 |
| 2008/0037367 A1 * | 2/2008 | Gross | A61B 5/0059 367/8 |
| 2008/0094633 A1 * | 4/2008 | Dimarzio et al. | 356/450 |
| 2008/0198432 A1 * | 8/2008 | Tanaka et al. | 359/32 |
| 2009/0009834 A1 * | 1/2009 | Yaqoob | G03H 1/0005 359/9 |
| 2009/0080313 A1 * | 3/2009 | Shimada et al. | 369/103 |
| 2010/0059696 A1 * | 3/2010 | Heintzmann | G02B 21/0056 250/550 |

FOREIGN PATENT DOCUMENTS

| | | |
|---|---|---|
| CN | 1973324 A | 5/2007 |
| JP | H01-178267 A | 7/1989 |

OTHER PUBLICATIONS

Nirmaier et al., "Very fast wave-front measurements at the human eye with a custom CMOS-based Hartmann-Shack sensor", Optics Express, vol. 11, No. 21, pp. 2704-2716 (Year: 2003).*
Qian Xiaofan, Zhang Lei, Dong Keping; "Phase Reconstruction of Cells with Microscopy Digital Holography Based on Phase Shifting Technique;" Acta Photonica Sinica, vol. 35, No. 10, Oct. 2006, pp. 1565-1568.

* cited by examiner

APPARATUS AND METHOD FOR IRRADIATING A MEDIUM

CROSS-REFERENCE TO RELATED APPLICATIONS

The present application is a Continuation of U.S. patent application Ser. No. 12/566,592 filed on Sep. 24, 2009 which has issued as U.S. Pat. No. 9,057,695 on Jun. 16, 2015. U.S. patent application Ser. No. 12/566,592 is hereby incorporated by reference herein in its entirety.

BACKGROUND OF THE INVENTION

Field of the Invention

The present invention relates to an apparatus and a method for irradiating a medium.

Description of the Related Art

Light scattering is one of the essential matters that can obstruct and even prevent viewing inside of, or through, a medium where scattering processes are dominant. This is because the scattered light does not propagate in a straight line through the medium, with the random paths of the scattered light causing the loss of directionality of the light as well as information associated therewith. Thus, it can be difficult to extract detailed internal information about a medium in which such scattering occurs via the detection of the scattered or diffused visible light. For example, in medical applications that deal with biological tissues, the scattering that occurs in passing light through the tissues may make it difficult to obtain internal information via detection of the scattered light.

In addition, there is also increasing demand to be able to concentrate light energy at a target position in a scattering medium, such as for example to allow for treatment of abnormal tissue in photodynamic therapy, as well as to achieve unique and promising functions that were heretofore unobtainable in intentionally disordered random materials.

The ability to focus light at a point inside of or through a scattering medium has not been achieved until fairly recently. However, in recent years, a technique has been proposed which optimizes a wavefront of incident light to suppress the scattering effect.

In U.S. Patent Application Publication No. 2009/0009834, an optical phase conjugation technique is disclosed that can be used to record a wavefront of scattered light transmitted through a scattering medium by a holographic recording material, and to generate a phase conjugation wave, which has a phase substantially opposite to the phase of the recorded wavefront. The phase conjugation wave is generated such that it is configured to enter the scattering medium and to be viewable through the scattering medium.

Since elastic optical scattering is a deterministic and time-reversible process, the optical phase conjugation can retrace its trajectory back through the scattering medium to its original incident point. The method as disclosed in U.S. Patent Application Publication No. 2009/0009834 utilizes this ability, which can be effective in suppressing the scattering effect and enhancing the spatial resolution of the images obtained of the scattering medium.

However, U.S. Patent Application Publication No. 2009/0009834 discloses that the optical phase conjugation method described therein is only capable of focusing light at a region just behind the scattering medium, where the incident light originally impinges. Therefore, as described therein, the method is not being capable of focusing light arbitrarily at any specific point inside the scattering medium. However, U.S. Patent Application Publication No. 2009/0009834 further suggests that it may be possible to use the phase conjugation method described therein to illuminate some of the specific scatterers that cause strong forward scattering inside the medium.

This situation, however, is applicable only when the scattering property of the medium is so low that it can be assumed that scattering occurs only at a few specific points in the medium where strong scatterers are located. In addition, the specific points (locations) may need to be known to be able to take advantage of this focusing effect in further applications such as imaging or therapy.

In many cases, such as in a high scattering medium including biological tissues, this situation is not practical. For example, in a strong scattering medium, the multiple scattering processes that can occur therein may make it quite difficult to specify which scatterers are dominant and are mainly responsible for causing the forward scattering (and sometimes the scattering may not even be in the forward direction). It can thus be difficult to retrace and illuminate the light path created by the multiple scattering processes using optical phase conjugation. Such multiple scattering processes may be caused, for example, by the presence of too many of the scatterers in the medium.

Furthermore, it can be challenging to determine the exact location where the optical phase conjugation retraces to focus in such a scattering medium, because the location of the "strong scatterers" inside the medium are usually not known, even when the light is focused in a general vicinity of the "strong scatters".

Thus, these points are of consideration in applying a phase conjugation method in a scattering medium.

SUMMARY OF THE INVENTION

Embodiments of the present invention provide an apparatus and a method for irradiating a medium.

According to an aspect of the present invention, an apparatus includes a first irradiating unit, including an electromagnetic wave source which emits an electromagnetic wave, to irradiate a medium with the electromagnetic wave which is scattered in the medium; an ultrasound device which transmits an ultrasonic wave to the medium to modulate a frequency of the electromagnetic wave at a position in the medium; and a second irradiating unit to irradiate a holographic material with a reference wave to record information corresponding to an interference pattern generated by interference between the modulated electromagnetic wave and the reference wave. The first irradiating unit, after the information is recorded on the holographic material, is configured to irradiate the holographic material so that the holographic material generates a reconstructed wave which irradiates the medium at the position in the medium.

According to another aspect of the present invention, an apparatus includes a first irradiating unit including a first electromagnetic wave source to irradiate a medium with an electromagnetic wave which is scattered in the medium; an ultrasound device which transmits an ultrasonic wave to the medium to modulate a frequency of the electromagnetic wave at a position in the medium; a second irradiating unit to irradiate a holographic material with a reference wave to record information corresponding to an interference pattern generated by interference between the modulated electromagnetic wave and the reference wave; and a third irradiating unit including a second electromagnetic wave source to irradiate the holographic material so that the holographic material generates a reconstructed wave which irradiates the medium at the position in the medium.

According to another aspect of the present invention, a method includes irradiating a medium with an electromagnetic wave which is scattered in the medium and modulated in frequency at a position in the medium; obtaining information corresponding to an interference pattern generated by interference between the modulated electromagnetic wave and a reference wave; and generating a phase conjugate wave, based on the obtained information, which irradiates the medium.

According to another aspect of the invention, an apparatus includes an irradiator including an electromagnetic wave source which emits an electromagnetic wave to irradiate a medium with the electromagnetic wave which is scattered in the medium; a modulator to modulate a frequency of the electromagnetic wave at a position in the medium; a detector to obtain information corresponding to an interference pattern generated by interference between the modulated electromagnetic wave and a reference wave, and a generator to generate a phase conjugate wave, based on the obtained information, which irradiates the medium.

Further features of the present invention will become apparent from the following description of exemplary embodiments with reference to the attached drawings.

DESCRIPTION OF THE EMBODIMENTS

Embodiments according to the present invention will be described below with reference to the attached drawings.

Figure 1A:
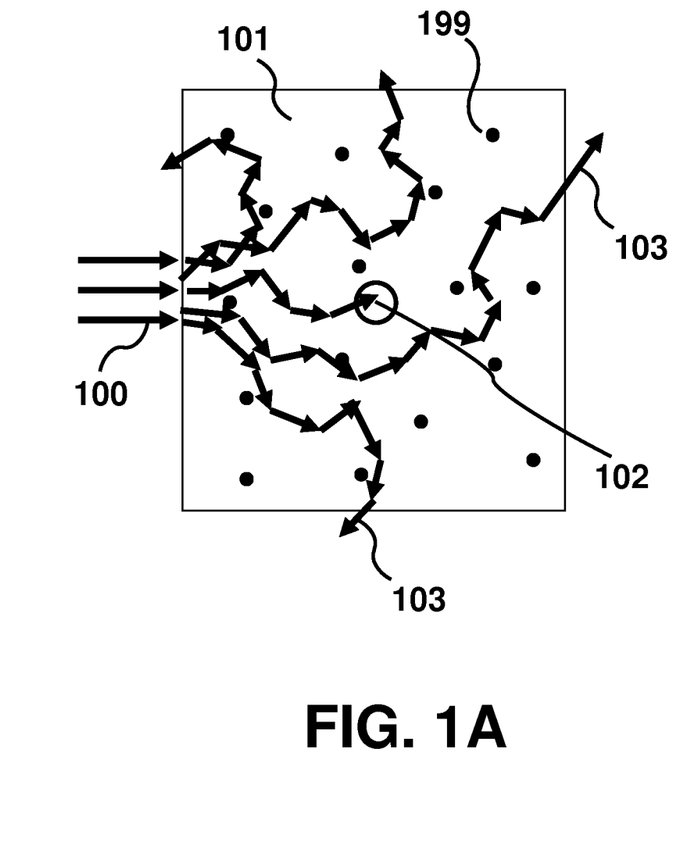
FIG. 1A illustrates multiple scattered light in a scattering medium.

FIG. 1A illustrates multiple light scattering and a position 102 in a scattering medium 101. At the position 102, a frequency of an incident light beam 100 can be modulated. Once the incident light beam 100 enters the scattering medium 101 including scattering particles 199, the light 100 undergoes multiple scattering throughout the propagation in the medium 101 and eventually exits from the surface of the medium 101 as scattered light 103. At this time, a portion of the incident light 100 can reach the position 102 and can be modulated in frequency at the position 102. For example, an ultrasonic wave can be employed to modulate the frequency of the incident light 100 at the position. Alternatively, a means which can modulate a frequency of the incident light at a local position in the medium may be available instead of the ultrasonic wave.

In a technique called acousto-optic imaging or ultrasound modulated tomography, when a scattering medium 101 is irradiated by an ultrasonic wave, the refractive index of the medium is modulated and in addition, the displacement of the scatterers in the scattering medium 101 is induced with the frequency of the applied ultrasonic wave. Once the portion of the incident light 100 reaches an ultrasound irradiated volume at the position in the medium 101, the optical phase of the light can be modulated by the frequency of the ultrasonic wave, and that causes frequency-shift of the light.

Figure 1B:
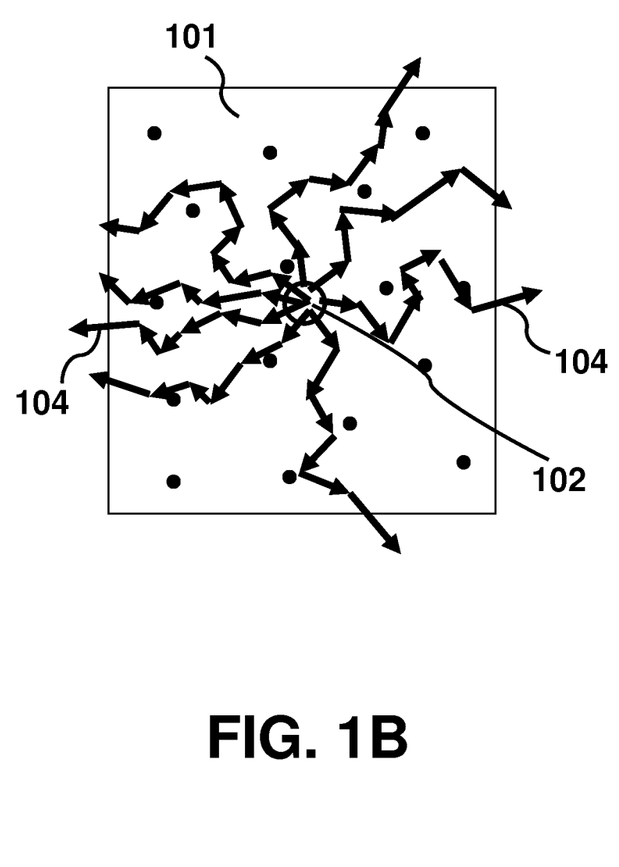
FIG. 1B illustrates "reemission" of frequency-shifted light in a scattering medium.

FIG. 1B illustrates the generation and propagation of interacted (frequency-shifted) light 104 in the medium 101. The frequency of the interacted light 104 is shifted (modulated) by the frequency of the ultrasonic wave. Therefore, the frequency of the light 104 is different from the incident light 100 and the scattered light 103 that is not modulated by the ultrasonic wave. This frequency-shifted light 104 originating from the ultrasound irradiated volume at the position 102 keeps propagating while undergoing multiple scattering and exits from the medium 101.

In other words, the ultrasound irradiated volume at the position 102 might act as if there is another light source inside the scattering medium 101 that generates light whose frequency is different from the original one. This frequency-shifted light 104 clearly originates from the ultrasound irradiated volume at the position 102.

Figure 1C:
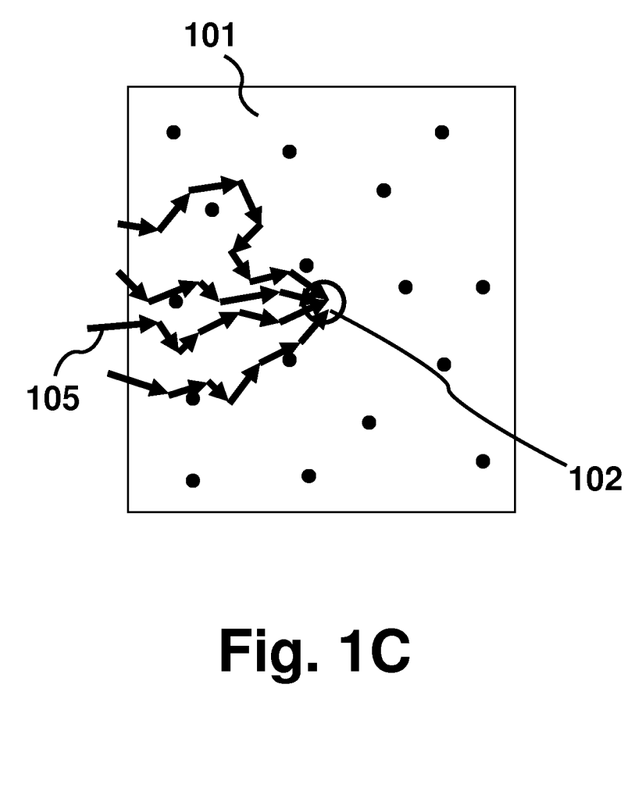
FIG. 1C illustrates light focusing in a scattering medium.

Once the wavefront corresponding mainly to this frequency-shifted light 104 is recorded and is played back with its phase conjugation 105, this phase conjugation can retrace its trajectory and reach or travel toward the position 102 shown in FIG. 1C. To realize a phase conjugation (i.e., a reconstructed wave, a phase conjugation wave), holography can be employed. In holography, an interference pattern generated by interference between the modulated light and a reference wave can be recorded in a holographic material, and also the interference pattern can be detected by a photodetector, such as a CCD sensor and a CMOS sensor. A technique to detect the interference pattern by the photodetector is referred to as digital holography. The phase conjugate wave can be generated based on the obtained information corresponding to the interference pattern. For example, when the interference pattern is recorded in the holographic material, the conjugate wave can be generated by a pump light, as is mentioned in a latter part herein. On the other hand, when the information is obtained by the array sensor, the conjugate wave can be generated by using a generator such as a spatial light modulator, as described in a fourth embodiment herein.

A method of focusing irradiation in a scattering medium may generally involve two steps. A first step is a recording step, and a second step is a reproducing (reconstructing) step.

Figure 2A:
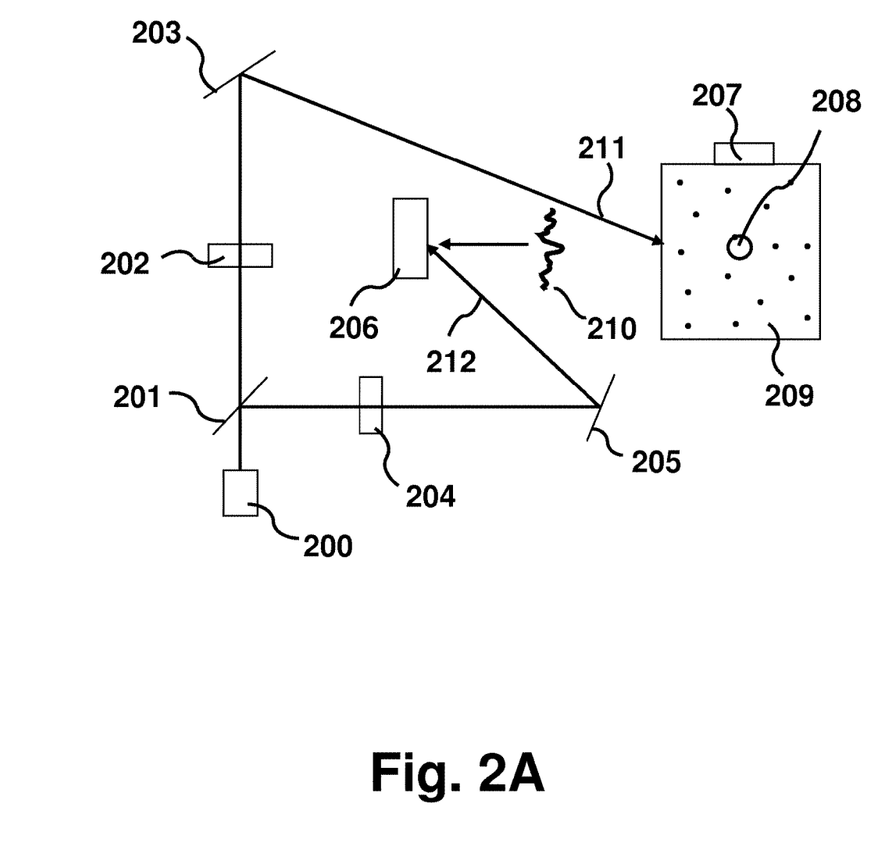
FIG. 2A illustrates an arrangement of a first step (recording process).

FIG. 2A shows an illustrative diagram of an arrangement for the first step. A coherent light source 200 emits an initial light beam. The initial light can be split into an incident light beam 211 and a reference light beam 212 by a beam splitter 201. Typically the wavelength emitted by the light source 200 can range from visible light (visible ray) to near-infrared light (near infrared ray). For example, an electromagnetic wave source that emits a wavelength from about 380 m to about 2500 nm, such as from 400 nm to 1500 nm, may be used as the light source 200.

External modulators such as acousto-optic modulators (AOM) 202 and 204 can be driven independently by clocks of frequencies which are adjusted such that the frequency difference between them is approximately equal to the frequency applied to an ultrasound system 207. For example, if the frequency of the AOM 202 is $f_1$ (=70 MHz) and the frequency of ultrasound is $f_a$ (=2 MHz), then the frequency $f_2$ of the AOM 204 is $f_1+f_a$ (=72 MHz). The incident light beam 211 and reference light beam 212 pass through the AOM 202 and AOM 204, respectively.

Another way to adjust the modulation frequency of those AOMs, is that AOM 202 may be placed on the reference light beam 212 path instead of on the incident light beam 211 path. Therefore, the reference light beam 212 can pass through the two AOMs while incident light beam 211 does not pass through the AOM. The frequency of the first AOM can be set at, for example, $f_1$=−70 MHz and the second one can be set at $f_2$=+72 MHz so that $f_1+f_2$=2 MHz, which is equivalent to the ultrasound frequency $f_a$ (=2 MHz). Alternatively, the two AOMs can be placed on the incident light beam 211 path instead of the reference light beam 212 path with the same frequency setting.

The ultrasound device 207 transmits an ultrasonic wave to create a focus volume 208 whose size and position may be determined a priori. It may be possible to radiate pulsed ultrasound to achieve small longitudinal focus volume. The pulse width of the ultrasound can be set depending on the size of the focus volume 208 and the speed of the ultrasonic wave in the scattering medium 209. Furthermore, stroboscopic irradiation can be used, where the timing of the irradiation from the light source 200 may be synchronized to irradiate the medium 209 only during the time period when the ultrasound pulse locates the position to be focused. To set the volume 208 at a position in the medium 209, a focused ultrasound may be employed.

A movable mirror 203 can be controlled and adjusted so that the incident light 211 enters the scattering medium 209. A first irradiating unit may comprise a system including the light source 200 to irradiate the medium 209, and optionally a controller to control the output of the light source 200. In the scattering medium 209, the incident light beam 211 is multiply scattered, and some portion of the light can reach the ultrasound focus volume 208 throughout the multiple scattering process and interact with ultrasound at a position of the volume 208.

The ultrasound focus volume 208 can re-emit the light as frequency-shifted light as a consequence of the interaction between the light and the ultrasound. At least a portion of the frequency-shifted light, as well as non-frequency-shifted light, reflects back and exits from the surface of the medium 209 where the incident light 211 entered. A signal light beam which exits from the surface of the medium 209 is shown as a scattered wavefront 210. The scattered wavefront 210 can also exit from a position different from a point where the incident light beam 211 entered. This wavefront 210 impinges onto a holographic material 206.

The reference light beam 212, which is adjusted to have the same frequency as that of frequency-shifted light by AOM 204, can be reflected by the mirror 205 to illuminate the holographic material 206. A second irradiating unit may comprise a system to irradiate the holographic material 206, such as the mirror 205.

The interference between the signal light beam, which includes both interacted and non-interacted light, and the reference light beam 212, generates an interferogram inside the holographic material 206. This interferogram may mainly consist of two components. One component is the interference between the non-frequency-shifted light and the reference light 212. The other component is the interference between the frequency-shifted light and the reference light beam 212.

The former interference component, formed by the different light frequencies, moves as the speed of the beat frequency that is the same as that applied to the ultrasound device 207. Typically this speed is so fast that the interference fringe is averaged out, and cannot be inscribed inside the holographic material 206. The latter interference component, formed by the same frequency, can create the static interference pattern inside the holographic material 206.

A bandpass filter may also be used to reject the non-frequency-shifted light and efficiently collect frequency-shifted light to form the hologram. For example, a Fabry-Perot interferometer, or a cryogenically-cooled spectral hole burning crystal, may be suitable. An array sensor, such as a CCD sensor or a CMOS sensor, can also be used to obtain information corresponding to the interference pattern, instead of the holographic material 206.

Consequently, the frequency-shifted light, which originates from the local ultrasound focus volume 208, can provide a main contribution in creating the static hologram in the holographic material 206. In other words, information corresponding to the interference between the reference light beam and the frequency-shifted light can be recorded in the holographic material 206.

Since a phase conjugation of light can retrace its trajectory, the phase conjugation of this inscribed wavefront can propagate back to the ultrasound focus volume 208. This means that an incident light which is the phase conjugation of the frequency-shifted light can focus back on the local volume 208 in the scattering medium 209.

Figure 2B:
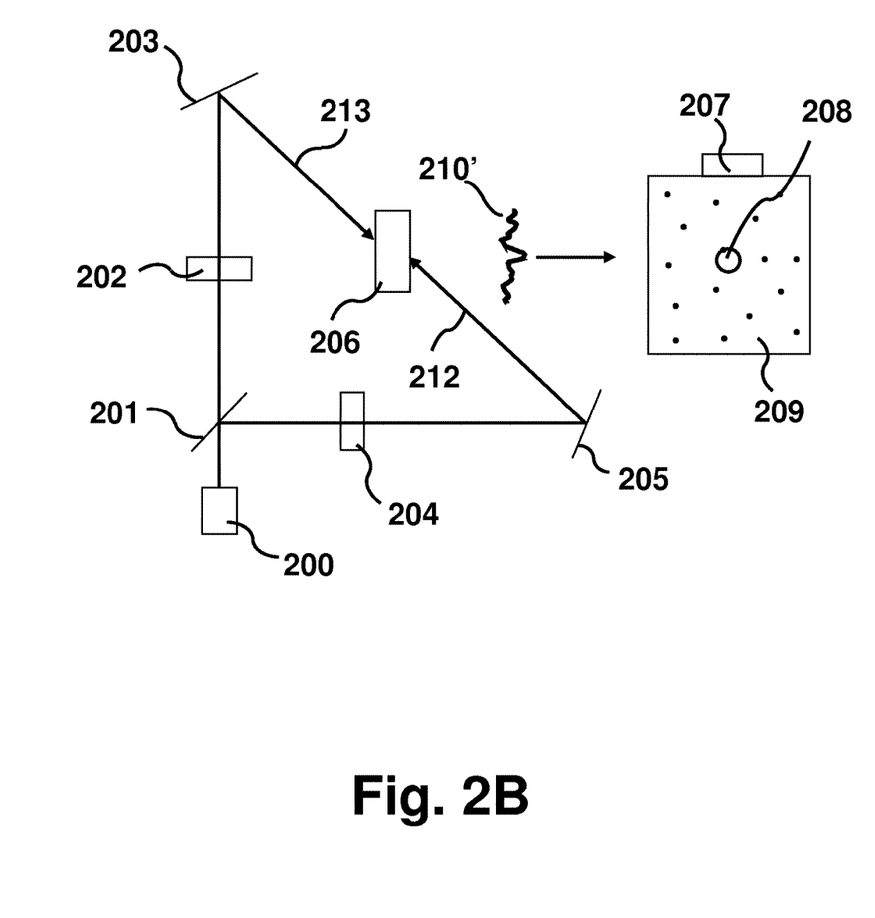
FIG. 2B illustrates an arrangement of a second step (reproducing process for irradiation).

FIG. 2B shows an illustrative diagram of an arrangement for the second step, which is a reproducing step to irradiate the volume 208.

The light emitted by the light source 200 eventually illuminates the holographic material 206 as a pump light beam 213 in a direction substantially opposite to that of the reference light beam 212, as shown in FIG. 2B. Alternatively, another light source for the pump light can also be employed instead of the light source 200, as described in a third embodiment. The first irradiating unit, after the information is recorded on the holographic material, may thus be configured to irradiate the holographic material without passing through the medium 209. The pump light beam 213 may be a continuous wave or a pulse wave.

This pump light generates a phase conjugation wave 210' of the recorded wavefront inside the holographic material 206. The phase conjugation wave 210' propagates toward the scattering medium 209 and enters the medium 209. This phase conjugation wave 210' can retrace its original trajectory experienced at the recording step in the scattering medium 209, and go back to the ultrasound focus volume 208. As a result, this local volume 208 can be focused by the phase conjugation light 210'. In other words, the holographic material may generate a reconstructed wave which irradiates the medium at the position in the medium, and the reconstructed wave may comprise the phase conjugate wave which travels to the position of the volume 208 in the medium 209. A controller, which controls an intensity of the reconstructed wave so that the intensity of the reconstructed wave is different from that of the electromagnetic wave 211 used to obtain the modulated electromagnetic wave 210, may be additionally employed. The controller can adjust the intensity of the light, for example, so that the reconstructed wave becomes weaker or stronger than the intensity of the electromagnetic wave 211 used to obtain the modulated electromagnetic wave 210 by using the controller. To detect a signal from the medium, a photodetector and/or an ultrasound detector may be used. The detector can be an image forming unit to form a tomographic image using the signal output from the medium 209 in response to an irradiation thereof by the reconstructed wave.

The properties of the ultrasound focus volume 208 (e.g., volume size, shape, position) are controllable by operating the ultrasound device 207 and its control unit (not shown). This feature may be quite important in a practical case. Therefore it may be possible to generate the phase conjugation wave which is capable of retracing to a specific local volume which is controllable inside the scattering medium. By applying this embodiment as either an irradiating apparatus or method in imaging which deals with multiple scattered light, the signal-to-noise ratio (SNR) of the output image may be enhanced. In addition, this embodiment may improve the measurement depth of that imaging method by focusing light inside the scattering medium. The irradiating method can be applicable to various kinds of imaging methods and other apparatuses that involve concentrating light in the scattering medium. The energy of the pump light beam 213 may also optionally be adjusted to be lower than energy of light used to create a hologram.

Here, the scattering medium can be, for example, a biological tissue or any other turbid medium or disordered material.

The holographic material 206 can be a conventional emulsion, or photorefractive crystal such as Lithium Niobate, Gallium Arsenide, BSO (Bismuth silicon oxide) or photorefractive polymer, for example, described in U.S. Pat. No. 6,653,421. Furthermore, a digital holography technique shown later may be applicable.

The intensity of the frequency-shifted light might be large enough to create the hologram for generating the phase conjugation wave. This intensity depends on the position of the medium and the size of the ultrasound focus volume 208 in the scattering medium 209. One of the possible ways to set up the ultrasound focus point 208 in order to focus light deep inside the scattering medium 209 may be to begin with that ultrasound focus point at a relatively shallower region where the frequency-shifted light is relatively easily detected to form the hologram.

As a next step, the ultrasound focus point 208 may be set at a point that is a little bit deeper in the medium where the frequency-shifted light still can be detected, even though the incident light is not sufficiently optimized to focus light, but is still better focused than ordinary irradiation. Once the newly developing hologram has been completed, the incident phase conjugation wave can focus on this new point in the scattering medium. By repeating this process step by step, the focus point can be deepened in the scattering medium.

Another way to deepen the ultrasound focus point may be to begin with a larger ultrasound focus volume, which is large enough to develop the hologram, and gradually reduce the ultrasound focus volume to a predetermined size.

Furthermore, in medical applications, for example to image (monitor) or to treat an abnormal tissue region using this embodiment, the ultrasound focus point may be set at the abnormal region by using a priori information provided by other modalities such as X-ray, MRI, ultrasound, or any other diagnostic results.

Figure 3A:
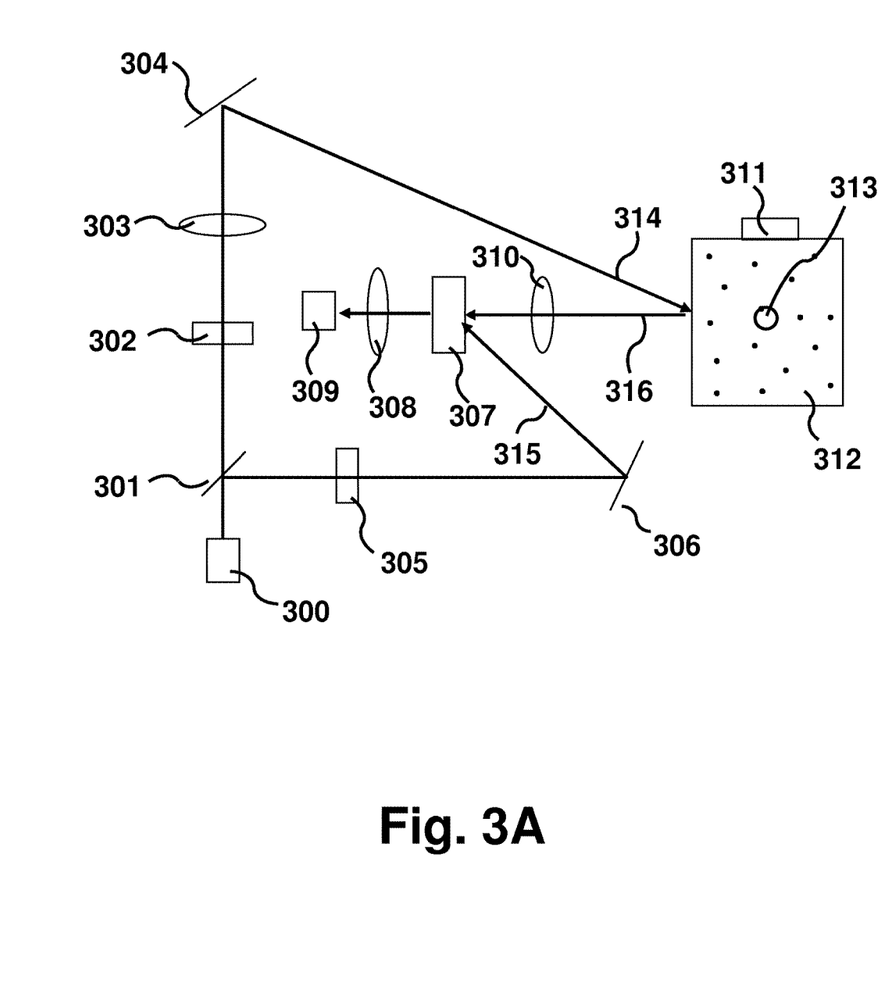
FIG. 3A illustrates an arrangement of a first step in an exemplary embodiment.
Figure 3B:
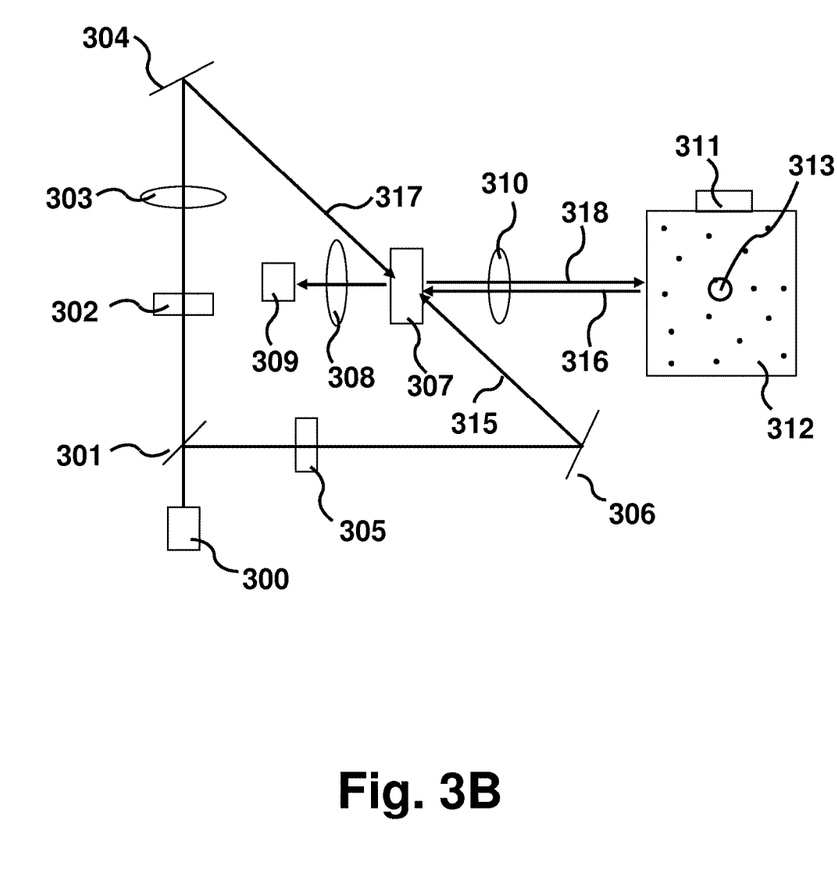
FIG. 3B illustrates an arrangement of a second step in the exemplary embodiment.

An irradiating apparatus and method according to a first embodiment of the present invention will be described below. FIGS. 3A and 3B are schematic diagrams illustrating an exemplary configuration of a recording step (FIG. 3A) and a reproducing step (FIG. 3B), respectively.

The first embodiment includes an acousto-optic imaging technique. A laser 300 emits an initial light and the initial light is split into an incident light beam 314 and a reference light beam 315 by a beam splitter 301 in FIG. 3A. The incident light beam 314 and the reference light beam 315 enter AOM 302 and AOM 305, respectively. The frequencies of those two AOMs are typically 50 MHz to 80 MHz, and are slightly different by an amount equal to the frequency applied to an ultrasound system 311, which ranges from approximately 1 to tens of megahertz. The role of these AOMs may be the same as described above.

A lens system 303 controls the beam size of the incident light 314, and a movable mirror 304 controls the incident point on the surface of a scattering medium 312. Once the incident light beam 314 enters the scattering medium 312, the light undergoes multiple scattering processes inside the medium 312.

The ultrasound system 311, which is acoustically matched to the medium 312, is operated in advance to form a focus volume 313 which is typically a few mm size at a position in the scattering medium 312. The ultrasound system 311 includes, for example, a linear array probe. Therefore the ultrasound focus volume 313 may be generated at any position in the scattering medium 312 by electronic focusing using the array probe. Alternatively, the ultrasound focus volume 313 may be provided at a desired position by mechanically scanning the ultrasound transducer, including a circular concave ultrasound transducer or a transducer including an acoustic lens. As such a transducer, a transducer using a piezoelectric phenomenon, a transducer using resonance of light, or a transducer using a change in capacity is available.

At least a portion of the incident light beam 314 may reach the ultrasound focus volume 313 and interact with ultrasound there. Some of the interacted light may reflect back to exit from the scattering medium 312 as frequency-shifted light 316. A lens system 310 collects the exiting scattered light onto a dynamic hologram device 307 such as a photorefractive crystal.

For example, the photorefractive crystal may be Lithium Niobate which has a size ranging from several millimeters to a few centimeters and a thickness greater than a few hundreds of micrometers to obtain sufficient diffraction efficiency.

The reference light beam 315, which has the same frequency as the frequency-shifted light 316, illuminates the photorefractive crystal 307 via a mirror 306 so that the reference light interferes with the frequency-shifted light 316. Consequently, the wavefront of the frequency-shifted light may be recorded as a static refractive index grating in the photorefractive crystal 307.

Subsequent illumination of the reference light beam 315 on the photorefractive crystal 307 after the creation of the hologram acts as a forward pump light. The forward pump light beam 315 is diffracted by the index grating creating inside the photorefractive crystal 307. This diffracted light and the frequency-shifted light 316 transmitted through the photorefractive crystal 307 interfere with each other and can be detected by a photodetector 309 through a collection lens system 308, for example as disclosed in U.S. patent application Ser. No. 2008/0037367. As for the photodetector 309, a single sensor such as a photomultiplier tube (PMT) or an avalanche photo diode (APD), can be used. Alternatively, a multi-sensor, such as a CCD or a CMOS, may be used. The photodetector 309 might be used to monitor the holographic material.

As the hologram is being formed, the output from the photodetector 309 may increase. After the creation of the hologram, that output signal does not increase. Therefore, by monitoring this output signal, it is possible to confirm the creation of the hologram inside the photorefractive crystal 307.

Meanwhile, the movable mirror 304 changes its angle so that the incident light beam 317 enters the photorefractive crystal 307 substantially in an opposite direction to that of the forward pump light beam 315 in FIG. 3B. This incident light beam 317 acts as a backward pump light, and generates the phase conjugation (phase conjugate wave) of the inscribed wavefront in the photorefractive crystal 307. This phase conjugation beam 318 propagates through the lens system 310 to enter the scattering medium 312.

Since the phase conjugation beam 318 can retrace its trajectory to the ultrasound focus volume 313 in the scattering medium 312, more and more light can enter this ultrasound focus volume 313 and interact with ultrasound. Therefore, much more frequency-shifted light 316 is reemitted from this local volume 313 and is detected through the photorefractive crystal 307 with lens systems 308, 310 and the photodetector 309 in FIG. 3B. As a result, the intensity of the frequency-shifted light which is the signal for acousto-optic imaging can be enhanced.

During the above whole measurement process, it may be possible that the ultrasound system 311 can continue to transmit the ultrasonic wave to form the focus volume 313, and the light beam 315 can continue to illuminate the photorefractive crystal 307 as a reference light as well as a forward pump light. At the same time, the backward pump light beam 317 can illuminate the photorefractive crystal 307 in a direction opposite to the pump light 315 to generate the phase conjugation beam 318.

In this kind of dynamic holographic method, the hologram which is inscribed in the photorefractive crystal 307 follows the change of its frequency-shifted wavefront self-adaptively. This adaptively changed hologram can help the phase conjugation beam 318 (having the phase conjugate wave) generated by the backward pump light 317 to focus the light in a slightly changed scattering environment in the medium 312. Especially in the case of biological tissues, the scattering environment, including the location of the scatterers, is changing as time advances, due mainly to biological activities. Since the wavefront of the frequency-shifted light at the reproducing step may be different from the wavefront at the recording step, this dynamic hologram method is effective due to self-adaptiveness to generate the phase conjugation in such a medium.

The power of the incident light beam 314 in FIG. 3A or the phase conjugation light beam 318 can be monitored and adjusted just before it enters the scattering medium (not shown in FIG. 3A and FIG. 3B). The power of the laser 300 can be controlled so that the input power is large enough to obtain the adequate frequency-shifted light in order to develop the hologram, which can be confirmed by the output signal from the photodetector 309, while keeping the power below the maximum exposure for safety when the scattering medium is a biological living tissue.

In addition, this system may change the intensity of the light between the recording process and the reproducing process. For example, at first, a relatively strong light intensity may be injected to obtain the frequency-shifted light 316 which is sufficient to create the hologram. Next, at the reproducing step, a relatively reduced intensity may be used as the backward pump light beam 317 to generate the phase conjugation beam 318, in order to save the power consumption while keeping sufficient SNR (signal-to-noise) due to the focusing effect.

Furthermore, the ultrasound focus volume 313 inside the scattering medium 312 may be scanned and each position of the volume may be sequentially subjected to the above process, thus obtaining an optical property distribution such as absorption and scattering in the medium 312 as described, for example, in U.S. Pat. No. 6,957,096. An image generating unit (not shown) can map these optical properties in accordance with the positions of the respective focus volume 313 to obtain a three-dimensional spatial distribution of those optical properties. A photodetector may be used to detect a signal output from the medium in response to an irradiation of the reconstructed wave.

Furthermore, the above-described process may be performed using a plurality of desired wavelengths of the laser source 300, and may optionally change the photorefractive crystal 307 to obtain functional information, such as a proportion of the constituents of the scattering medium 312, e.g., oxy-hemoglobin, deoxy-hemoglobin, water, fat, collagen and an oxygen saturation index of the medium 312, such as when the scattering medium 312 is a biological tissue for medical application. The following are hereby incorporated by reference in their entireties as though fully and completely set forth herein: U.S. Pat. No. 6,738,653 to Sfez et al, issued May 18, 2004, and U.S. Patent Application Publication No. 2008/0037367 to Gross et al, published Feb. 14, 2008.

An irradiating apparatus and method according to a second embodiment of the present invention will now be described. The configuration of an imaging system in this embodiment is same as that of in the first embodiment shown in FIG. 3A and FIG. 3B, except for adding photodetectors around the scattering medium 312 (not shown). The imaging system in the second embodiment includes a technique called diffuse optical tomography (DOT).

The flow may also be the same as in the first embodiment until the hologram has been developed in the photorefractive crystal 307. Once the hologram has been created in the photorefractive crystal 307, the backward pump light beam 317 illuminates the photorefractive crystal 307 to generate the phase conjugation beam (including the phase conjugate wave) 318. At this moment, the ultrasound system 311 may be turned off to perform DOT measurement.

After this phase conjugation beam 318 enters the scattering medium 312, it can retrace to the ultrasound focus volume 313 and furthermore retrace back to the original incident point. The photodetectors placed adequately around the scattering medium 312 can detect the exiting scattered light. It may be possible to restrict or decrease the light paths inside the scattering medium 312 by controlling the position of the ultrasound focus volume 313 while taking advantage of techniques used in DOT. Therefore, this imaging system may serve to reduce the ill-posedness, which is one of the problems in DOT. As described in the embodiment, when the light is focused on a position in a scattering medium, it may become easier to analyze a signal output from the medium in response to a focused irradiation.

By repeating the above measurement process with different incident light points, the system can collect data to reconstruct the images of the internal distribution of optical properties such as absorption, and as in DOT. The image forming system (not shown) reconstructs those images based on the measurement data to obtain three-dimensional images of absorption and scattering properties distribution inside the medium 312.

It may also be possible that measurement is performed at a plurality of wavelengths to obtain spectral information, as in the first embodiment, to extract functional information of the biological tissues.

Here, it is possible to perform time-domain measurement by using a pulse laser at an irradiating step and a time-correlated photon counting system (not shown), or to perform frequency-domain measurement by modulating the intensity of the laser 300 output and for example, lock-in detection system (not shown). The following are hereby incorporated by reference in their entireties as though fully and completely set forth herein: U.S. Pat. No. 5,441,054 to Tsuchiya, issued Aug. 15, 1995, U.S. Pat. No. 5,477,051 to Tsuchiya, issued Dec. 19, 1995, U.S. Pat. No. 5,517,987 to Tsuchiya, issued May 21, 1996, and U.S. Pat. No. 5,424,843 to Tromberg et al, issued Jun. 13, 1995.

Figure 4:
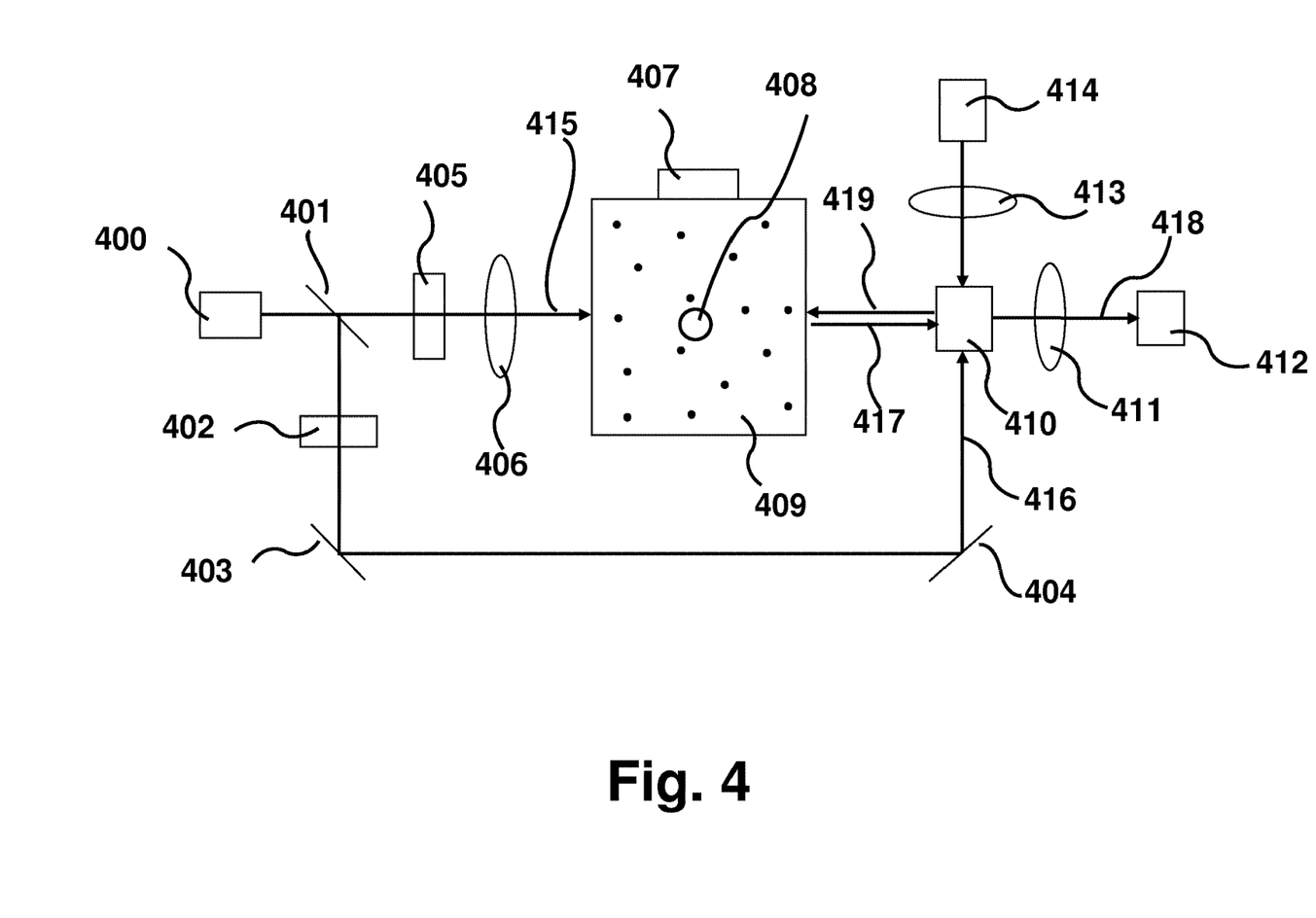
FIG. 4 illustrates an arrangement of another exemplary embodiment.

An irradiating apparatus and method according to a third embodiment of the present invention will be described. FIG. 4 is a schematic diagram illustrating an exemplary configuration of an imaging system with the irradiating apparatus according to the embodiment. The system of this embodiment may include two combined systems, which are an acousto-optic imaging system and a photoacoustic imaging system.

A laser source 400 (a first electromagnetic wave source as a part of a first irradiating unit) emits initial light and is split into an incident light beam 415 and a reference light beam 416 by a beam splitter 401. An AOM 402 and AOM 405 have a same role as already described above to adjust the frequency. The incident light beam 415 enters a scattering medium 409 through an optical system 406.

An ultrasound system 407 including an ultrasound device, which may be acoustically matched to the medium 409, controls an ultrasound focus volume 408 with size and position inside the scattering medium 409. At least a portion of the frequency-shifted light 417 originating from the local volume 408 exits from the scattering medium 409 and impinges onto a photorefractive device 410 to create a hologram by interfering with the reference light beam 416 reflected from a mirror 403 and 404 (as a part of a second irradiating unit).

During the creation of the hologram inside the photorefractive device 410, the acousto-optic signal 418, which is the frequency-shifted light, can be monitored by a photodetector 412 through a collection lens system 411 to confirm the development in the same way as described above in the first embodiment. At this time, this frequency-shifted light signal is stored into a memory (not shown) to be used for reconstructing images.

Once the creation of the hologram has been completed, a third irradiating unit comprising a pulse laser source 414 (a second electromagnetic wave source) for photoacoustic imaging emits a pulse light of several nanoseconds. The pulse light illuminates the photorefractive device 410 substantially in an opposite direction to the reference light beam 416 to generate the phase conjugation of the frequency-shifted wavefront inscribed in the photorefractive device 410. The phase conjugation beam (including the phase conjugate wave) 419 propagates backward to the scattering medium 409.

The ultrasound system 407 can change its operation mode from a transmission mode to a reception mode in order to detect a photoacoustic signal, without changing the focusing setting used for the transmission mode.

Since the incident phase conjugation beam 419 can retrace the trajectory to the local volume 408 in the scattering medium 409, this incident light beam 419 can focus at the local volume 408 that is the measurement volume for photoacoustic imaging.

The energy of the light absorbed in the local volume 408 locally causes an increase in temperature, thus resulting in expansion of the volume of this local region and an acoustic wave (photoacoustic signal) is generated. According to the equation (1), the photoacoustic signal P is proportional to the local absorption coefficient $\mu_a$ and light fluence rate $\Phi$ at that point.

$$P = \Gamma \mu_a \Phi \quad (1)$$

where $\Gamma$ is Grueneisen coefficient (heat–acoustic conversion efficiency).

Therefore, a higher fluence rate generates a larger photoacoustic signal. Since the incident phase conjugation beam 419 can focus light at the local volume 408, a larger photoacoustic signal is generated from this local volume 408. The ultrasound system 407 which is set to focus that volume 408 in the reception mode detects the photoacoustic signal originated from that volume 408. Alternatively or additionally, another ultrasound detector may be provided to detect a signal output from the medium 409 in response to an irradiation by the reconstructed wave 419.

Figure 5:
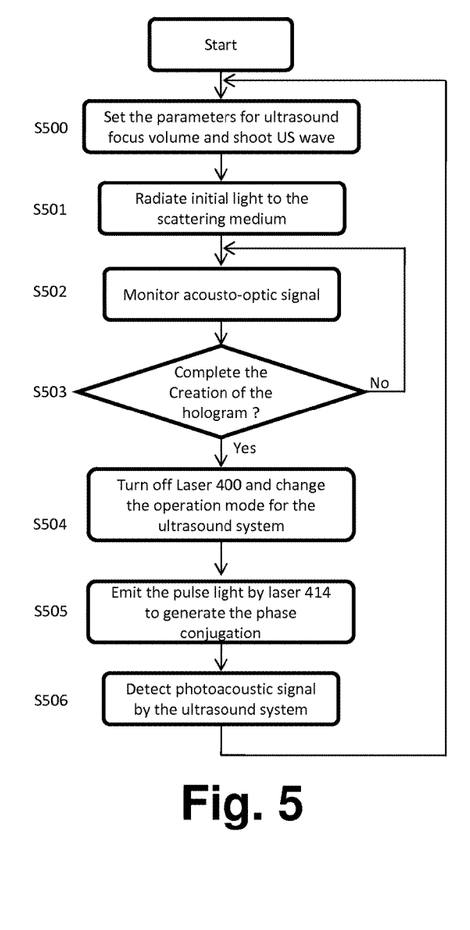
FIG. 5 illustrates an exemplary operation flow.

FIG. 5 shows an exemplary operation flow of this system. At first, the parameter conditions regarding the focus of the ultrasound system 407, such as the size or the position of the focus volume, is set at S500, and then the ultrasound system 407 transmits pulsed ultrasonic waves to form the ultrasound focus volume 408. At S501, the laser 400 radiates the initial light beam.

Through the acousto-optic imaging, the acousto-optical signal (frequency-shifted light) is monitored by the photodetector 412 at S502, and the photodetector 412 confirms whether or not the creation of the hologram is completed at S503. These processes at S502 and S503 may be repeated until the creation of the hologram is confirmed. In addition, before moving to S504 after completing the hologram, the acousto-optical signal can be stored.

Once the hologram has been developed, then the laser 400 is turned off and the operation mode for the ultrasound system 407 is changed from a transmission mode to a reception mode at S504. After that, the laser 414 radiates a pulsed light beam to the photorefractive device 410 at S505 in substantially an opposite direction to the reference light beam 416 to generate the phase conjugation light beam 419. At S506, the photoacoustic signal is detected by the ultrasound system 407.

This is an exemplary basic operation flow, and if the measurement position for photoacoustic imaging needs to be changed, the ultrasound system may change its focus position and go back to S500 and repeat the entire flow (S500 to S506).

An image generating process may follow the measurement. An image generating unit (not shown) may reconstruct three-dimensional images by using the above data. The image generating unit maps an absorption signal obtained by photoacoustic measurement in accordance with the positions of the ultrasound focus volume 408. At this time, an acousto-optic signal stored at S503 is read and used to generate a scattering distribution image in the same way. Since photoacoustic image is sensitive to absorption, while acousto-optic image is sensitive to scattering, by combining both measurement results, absorption and scattering distribution images can be generated.

Furthermore, it is possible to add one more step before S500. That is, a pulsed ultrasonic wave may be transmitted from the ultrasound system 407 and an ultrasonic echo, serving as a reflected wave, may be received by the ultrasound system 407. This ultrasound echo measurement may be performed while the direction in which the pulse ultrasonic wave is transmitted is changed relative to the scattering medium 409, thus obtaining structural data regarding the inside of the scattering medium 409. The ultrasound focus volume 408 can be set by taking advantage of the structural data obtained by the ultrasound echo measurement, for example, by setting at a position where a characteristic difference can be seen in the echo image.

Alternatively, it may possible to select the measurement point of photoacoustic imaging by analyzing an acousto-optic signal obtained and stored at S503. At first, an acousto-optic imaging system may be used to find an area to be measured by the photoacoustic system. If distinctive changes are found in the acousto-optic signal, then the laser 414 for photoacoustic imaging emits pulse light. Or it may be also possible to use the photoacoustic imaging system to search the characteristic region instead of using the acousto-optic imaging system before deciding the ultrasound focus volume 408.

The imaging system of this embodiment can also be achieved with the configuration shown in FIGS. 3A and 3B. In this case a light source unit 300 may emit light from at least two different lasers. One may be a laser for an acousto-optic system and the other may be a pulse laser for a photoacoustic system. The lasers can be switched from one to the other between the recording step and the reproducing step.

By focusing light at the measurement volume of photoacoustic imaging, it may be possible to enhance the measurement depth and SNR of photoacoustic imaging. The following are hereby incorporated by reference in their entireties as though fully and completely set forth herein: U.S. Pat. No. 4,385,634 to Bowen, issued May 31, 1983, U.S. Pat. No. 5,840,023 to Oraevsky et al, issued Nov. 24, 1998, and U.S. Pat. No. 5,713,356 to Kruger, issued Feb. 3, 1998. An imaging system including two combined systems which are an acousto-optic imaging system and a photoacoustic imaging system may be realized to obtain a clearer image or a useful image for diagnosis.

Figure 6:
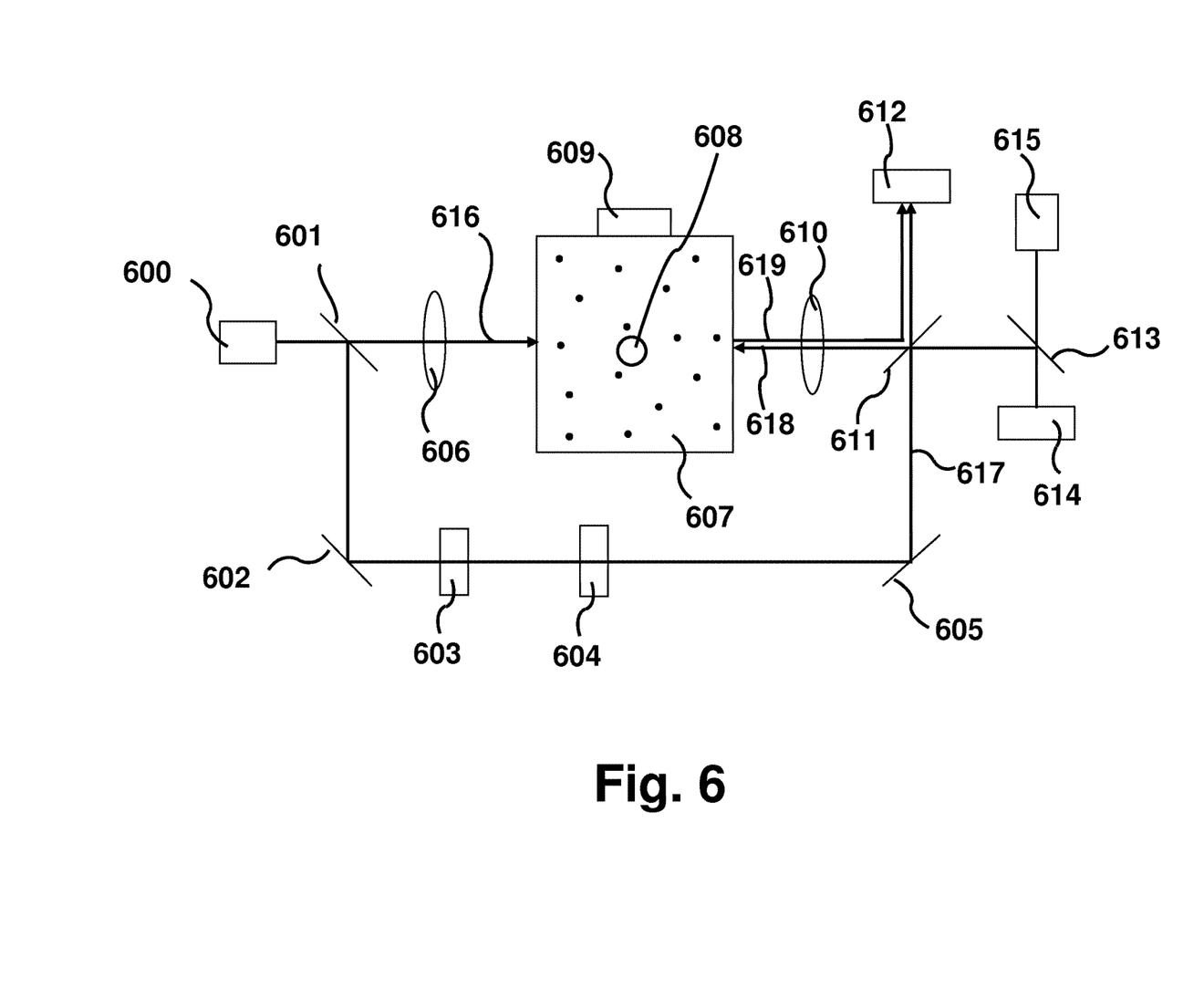
FIG. 6 illustrates an arrangement of another exemplary embodiment.

An irradiating apparatus and method according to a fourth embodiment of the present invention will be described. FIG. 6 is a schematic diagram illustrating an exemplary configuration of a light irradiating apparatus to deliver light into a specific position in a disordered scattering material.

An irradiator comprising a laser source 600 emits an initial light beam which is split into an incident light beam 616 and a reference light beam 617 by a beam splitter 601. A lens system 606 expands the incident light beam 616 to irradiate the material 607. AOMs 603 and 604, and mirrors 602 and 613 may be placed on the path of the reference light beam 617 so that the frequency of the reference light can be adjustable.

A modulator comprising an ultrasound system 609 may be acoustically matched to the material 609 and irradiate the ultrasonic wave. An ultrasound focus volume 608 is formed in the material 607 by the ultrasound system 609.

As already described above, some of the frequency-shifted light 619 originating from the focus volume 608 exits from the surface of the material 607 and is guided to a detector comprising a CCD sensor 612 through a lens system 610 and a dichroic mirror 611. Here, a COMS sensor or area sensors with an image intensifier, or EMCCD (Electron Multiplying CCD) are also applicable. The reference light beam 617 is reflected by a mirror 605 to reach the CCD 612 eventually to create a hologram, which is based on an interference between the reference light beam 617 and the frequency-shifted light 619 on the CCD 612.

A processing unit (not shown) is provided in this system. This processing unit controls a generator comprising a spatial light modulator (SLM) 614, such as a liquid crystal on silicon (LCOS), in order to generate a reconstructed light which may be equivalent to the phase conjugation (phase conjugate wave) by utilizing a digital holography technique.

The interferogram of the frequency-shifted light can be obtained by a phase-shifting digital holography technique. At the CCD 612 plane, non-frequency-shifted light, frequency-shifted light and the reference light are impinging. The frequency of the reference light ($f_R$) is adjusted, for example according to the following equation, by adjusting the AOM 603 and 604.

$$f_R = f_U + f_A + f_C/N \quad (2)$$

where, $f_U$ is the frequency of unshifted light, $f_A$ is the frequency of the ultrasound, $f_C$ is the frame rate of the CCD 612 and N is the number of measurements for phase shifting method. Since the CCD 612 acts as a low-pass filter, mainly the component of the interferogram between the frequency-shifted light 619 and reference light beam 617 carries the fringes, which varies slowly in time so that the CCD 612 can efficiently detect the interferogram (the digital hologram).

The phase distribution is obtained by calculating the phase of the detected frequency-shifted light on each pixel from the digital hologram with a phase-shifting method. The processing unit sets the phase value of each pixel in the SLM 614 according to the phase distribution obtained by the digital hologram. At this time, the difference of the optical length between the CCD 612 and the SLM 614 or any other system error may be calibrated, and the phase values may be corrected. Alternatively, the CCD 612 and the SLM 614 may be arranged so that the optical length from the exit plane of the material 607 to those devices is the same.

The SLM 614 modulates the phase of light emitted by a laser 615. This phase modulation develops a reconstructed light beam 618 which may be equivalent to the phase conjugation and can retrace the trajectory back to the ultrasound focus volume 608 in the material 607. The reconstructed light beam 618 developed by the SLM 614 is configured to irradiate the material 607. In case the apparatus may be used for creating an image inside the material, a signal output from the material that results from the irradiation of the material by the reconstructed light beam 618 can be detected to form the image, as already described in the other embodiment.

If the CCD 612 has a larger number of pixels compared to the SLM 614, the CCD 612 may perform binning so that the number of pixels between them is equal and those pixels are corresponding with each other.

Furthermore, any other digital technique used in the digital holography may be applied to improve the characteristic of the reconstructed light.

The irradiating apparatus described in the fourth embodiment can also be applicable to therapy or treatment such as photodynamic therapy in biological tissues. The configuration of the system in a fifth embodiment may be same as that shown in FIG. 6.

Once the digital hologram has been obtained and the SLM 614 is ready for the phase modulation in accordance with the digital hologram, the laser 615 can shoot light which has a relatively stronger power compared to the light emitted by the laser 600 used to create the digital hologram. The light power of the laser 615 can be controlled depending on the treatment.

Furthermore, many kinds of lasers can be applicable depending on the purpose of the therapy or treatment (e.g., femto second pulse to pico, nano, micro etc).

The reconstructed light beam 618 for therapy whose phase can be controlled by the SLM 614 can reach the ultrasound focus volume 608 to deliver light energy at that tissue region where the treatment is needed. The position of the ultrasound focus volume 608 may be set by referring to other diagnostic results.

By using the embodiment according to the present invention, it may be possible to deliver the high energy density of light efficiently to a specific point with less damage.

The described embodiments can also be applied to fluorescence imaging which uses a chemical probe (molecules) to obtain biochemical information such as abnormality of the tissue, for example, by setting the ultrasound focus volume to the point where the fluorescence probe is located. The reproducing step for irradiation thereof may be the same as already described above. If the location of the chemical probe is not certain, then the ultrasound focus volume can simply be scanned to irradiate inside the scattering medium one position at a time. By focusing light at the position where the fluorescence probe is located, it may be possible to obtain high contrast images of the target, such as for example a tumor.

As has already been described, the embodiments according to the present invention can be applicable to a variety of optical imaging or therapy or apparatuses for the purpose of concentrating light at specific points, which may be controllable, inside the scattering medium.

While the embodiments according to the present invention have been described with reference to exemplary embodiments, it is to be understood that the present invention is not limited to the above described embodiments. The scope of the following claims is to be accorded the broadest interpretation so as to encompass all such modifications and equivalent structures and functions.

What is claimed is:

1. An apparatus comprising:
   a first irradiation unit configured to irradiate a medium with an incident wave;
   an ultrasound device configured to focus an ultrasound wave onto a position in the medium such that the incident wave is modulated into a frequency-shifted wave at the position where the ultrasound wave is focused by the ultrasound device;
   a first detection unit configured to obtain information corresponding to an interference pattern generated by interference between the frequency-shifted wave and a reference wave;
   a second irradiation unit configured to irradiate the first detection unit with the reference wave, a frequency difference between the reference wave and the incident wave being exactly or approximately equal to a frequency of the ultrasound wave focused by the ultrasound device;
   a generation unit configured to irradiate the medium with a phase conjugation wave of the frequency-shifted wave to irradiate the medium to retrace trajectory of the frequency-shifted wave to the position where the ultrasound wave is focused by the ultrasound device based on the information obtained by the first detection unit; and
   a processing unit configured to control the generation unit,
   a second control unit configured to control the ultrasound device,
   wherein the first detection unit comprises an array sensor configured to detect the interference pattern,
   wherein the generation unit comprises a spatial light modulator,
   wherein the processing unit is configured set phase values of pixels included in the spatial light modulator based on the information corresponding to the interference pattern detected by the array sensor, and
   wherein the spatial light modulator is configured to modulate light by the set phase values at the pixels included in the spatial light modulator to generate the phase conjugation wave of the frequency-shifted wave,
   wherein the second control unit is configured to set the position by using information obtained from a modality such that the ultrasound device focuses the ultrasound wave onto the set position, the modality including X-ray, MRI, or ultrasound.

2. The apparatus according to claim 1, further comprising:
   a first photodetector arranged to monitor an intensity of the incident wave before being irradiated on the medium, and
   a first control unit configured to control the first irradiation unit and the generation unit so that an intensity of the phase conjugation wave generated from the generation unit is different from an intensity of the incident wave generated from the first irradiation unit,
   wherein the first control unit is configured to control the first irradiation unit based on an output of the first photodetector so that the intensity of the incident wave is kept below a predetermined exposure and is configured to control the generation unit so that the intensity of the phase conjugation wave is lower than the predetermined exposure.

3. The apparatus according to claim 2, wherein the predetermined exposure is a maximum exposure.

4. The apparatus according to claim 1, wherein the array sensor comprises a CCD sensor, a CMOS sensor, area sensors with an image intensifier, or EMCCD (Electron Multiplying CCD).

5. The apparatus according to claim 1, further comprising a second detection unit configured to detect a signal output from the medium in response to irradiation of the phase conjugation wave.

6. The apparatus according to claim 1, further comprising a second photodetector configured to detect a light signal output from the medium in response to irradiation of the phase conjugation wave.

7. The apparatus according to claim 1, further comprising an ultrasound detector configured to detect a photoacoustic signal output from the medium in response to irradiation of the phase conjugation wave.

8. The apparatus according to claim 1, wherein the ultrasound device is configured to detect a photoacoustic signal output from the medium in response to irradiation of the phase conjugation wave.

9. The apparatus according to claim 1, further comprising an image formation unit configured to form an image using a signal output from the medium in response to irradiation of the phase conjugation wave.

10. The apparatus according to claim 1, wherein the first irradiation unit and the second irradiation unit include a common electromagnetic wave source.

11. The apparatus according to claim 1, wherein the common electromagnetic wave source is configured to generate an electromagnetic wave whose wavelength is not less than 380 nm and not more than 2500 nm.

12. The apparatus according to claim 1, further comprising a filter between the medium and the first detection unit, wherein
the filter reduces by a first amount an intensity of the first electromagnetic wave transmitted from the medium to the first detection unit;
the filter reduces by a second amount an intensity of the frequency-shifted electromagnetic wave transmitted from the medium to the first detection unit; and
the first amount is greater than the second amount.

13. The apparatus according to claim 1, wherein the first detection unit is configured to obtain the information corresponding to the interference pattern by a phase-shifting digital holography technique, the frequency difference between the reference wave and the incident wave being exactly or approximately equal to a sum of a frequency of the ultrasound wave focus by the ultrasound device and a value which is a frame rate of the first detection unit divided by a number of measurements for a phase shifting method.

14. The apparatus according to claim 1, the first irradiation unit includes a modulator configured to modulate a frequency of the incident wave.

15. The apparatus according to claim 1, wherein the second irradiation unit includes a modulator configured to modulate a frequency of the reference wave.

16. The apparatus according to claim 1, wherein the spatial light modulator comprises a liquid crystal on silicon.

17. The apparatus according to claim 1, wherein,
in a case that the array sensor has a larger number of pixels compared to the spatial light modulator, the array sensor is configured to perform binning so that the number of pixels between the array sensor and the spatial light modulator is equal and those pixels correspond with each other.

18. The apparatus according to claim 1, wherein the second control unit is configured to set a first position and a second position that is deeper than the first position in the medium such that, after focusing of the reconstructed light on the first position, the reconstructed light is focused on the second position.

19. The apparatus according to claim 1, wherein the second control unit is configured to set a first size and a second size that is smaller than the first size of a focus region of the ultrasound wave such that, after focusing of the reconstructed light on the focus region of the first size, the reconstructed light is focused on the focus region of the second size.

* * * * *